United States Patent [19]

Cooper

[11] Patent Number: 4,904,270
[45] Date of Patent: Feb. 27, 1990

[54] HIP JOINT FOR PROSTHETIC LEG

[75] Inventor: John E. Cooper, Surrey, United Kingdom

[73] Assignee: J. E. Hanger & Company Limited, London, United Kingdom

[21] Appl. No.: 172,363

[22] Filed: Mar. 24, 1988

[30] Foreign Application Priority Data

Mar. 27, 1987 [GB] United Kingdom ................ 8707378

[51] Int. Cl.$^4$ .............................................. A61F 2/80
[52] U.S. Cl. ......................................... 623/38; 623/27
[58] Field of Search ...................... 623/31, 38, 47, 48, 623/27, 66, 39; 403/DIG. 8, 160, 4, 409

[56] References Cited

U.S. PATENT DOCUMENTS

| | | | |
|---|---|---|---|
| 3,538,516 | 11/1970 | Bailey et al. | 623/38 |
| 3,671,978 | 6/1972 | May | 623/66 X |
| 3,806,958 | 4/1974 | Gusev | 623/44 X |
| 4,513,457 | 4/1985 | Glabiszewski | 623/31 |
| 4,727,861 | 3/1988 | Yeomans et al. | 623/39 X |

FOREIGN PATENT DOCUMENTS

| | | | |
|---|---|---|---|
| 135800 | 5/1979 | Fed. Rep. of Germany | 623/38 |
| 2410998 | 8/1979 | France | 623/38 |
| 2092451 | 8/1982 | United Kingdom | 623/47 |

Primary Examiner—Richard J. Apley
Assistant Examiner—H. N. Flaxman
Attorney, Agent, or Firm—Shoemaker and Mattare, Ltd.

[57] ABSTRACT

A hip joint for a prosthetic leg has first and second members pivoted together by a pin through the first member. The pin includes an outer spool-like spindle roatable in a bearing in said first member and an inner spool-like spindle rotatable in a bearing in the outer spindle and carrying pivots for the second member. The inner spindle has an axis skew to the outer spindle so that firstly an angle may be set between the pivot axis of the joint and said first member by adjusting the relative angular positions of the inner and outer spindles and secondly an attitude of said pivot axis may be set by adjusting the angular position of the outer spindle relative to the first member. The hip joint may have a buffer assembly that contacts an abutment on the first member at a contact line or plane to define a rearward limit of swing of the second member. The buffer assembly may have a first adjustment mechanism by which a limit of swing of the second member can be set and a second adjustment mechanism by which a line or plane or action of the buffer assembly can be aligned with the abutment on the first member. A stride limiter carried by the second member is also described.

16 Claims, 6 Drawing Sheets

FIG.11a. REQUIRED

FIG.11b. AVAILABLE

FIG.11c. COMBINED

HIP JOINT FOR PROSTHETIC LEG

FIELD OF THE INVENTION

This invention relates to a hip joint for a prosthetic leg.

SUMMARY OF THE INVENTION

More particularly, the invention provides a hip joint as aforesaid, wherein first and second members are pivoted together by a pin through one of the members, the pin including outer spindle means rotatable in a bearing in said first member and inner spindle means rotatable in a bearing in said outer spindle means and carrying pivot means for said second member, said inner spindle means having an axis skew to the outer spindle means so that firstly an angle between the pivot axis of the joint and said first member may be set by adjusting the relative angular positions of said inner and outer spindle means and secondly an attitude of said pivot axis may be set by adjusting the angular position of said outer spindle means relative to said first member.

DESCRIPTION OF PREFERRED FEATURES

Means may be provided for locking the relative positions of said first and second spindle means and said first member once the required positions have been established.

The first member is conveniently a hinge knuckle, in which case the second member is a fork connected to the knuckle by a pin. A base of the the fork may then have a socket for receiving a thigh tube of the prosthetic leg.

The inner spindle means may have a bore in which a pair of stub shafts fit, means retaining the stub shafts in the bore, said stub shafts fitting into bearings in the second member. The retaining means may be a screw inserted through a bore in one stub shaft into a threaded bore in the other stub shaft. The other stub shaft may then be coupled to the inner spindle means for rotation therewith and may have a formation for receiving a tool by which said stub shaft may be rotated. For convenience of assembly, the outer spindle means may be in the form of a spool having flanges that locate against the first member at opposed ends of the bearing therein, the inner spindle means then being also in the form of a spool having flanges that locate against the flanges of the outer spindle means. The outer spindle means and the inner spindle means are advantageously then each formed in two complementary parts that fit together from opposed sides of the bearing in the first member, means coupling the complementary parts so that they rotate together. One complementary part may be a flanged sleeve whilst the other complementary part is a washer.

Normally in a hip joint as aforesaid, the second member carries buffer means that contacts an abutment on the first member at a contact line or plane to define a rearward limit of swing of the second member, the buffer assembly having first adjustment means by which a limit of rearward swing of the second member can be set and second adjustment means by which a line or plane of action of the buffer assembly can be aligned with the abutment on the first member. In a conveniet form of said buffer means, the second member has a medially-laterally directed buffer bar having a pivot at its centre, a first screw jack having an end connected by the pivot to the buffer bar, extension or retraction of the first screw jack varying the distance of the buffer bar pivot from the second member, and second and third screw jacks in the second member to either side of the first screw jack acting adjacent the ends of the buffer bar, the arrangement being such that with the first screw jack extended the attitude of the buffer bar can be set parallel to the plane of the abutment of the first member by extension or retraction of the second and third screw jacks, and the first screw jack can be re-tightened to hold the buffer bar in compression against the second and third screw jacks.

Line or plane contact is ensured if, as is preferred, the buffer bar carries a buffer shoe of elastomeric material that is convexly curved when viewed in profile.

For ease of adjustment of a buffer bar as aforesaid, the second member has a front face and first, second and third bores opening into said front face into which said first, second and third screw jacks fit, each screw jack having a socket or other formation by which it may be rotated and which is accessible from the front face of the second member.

Normally in a hip joint as aforesaid, there is provision for limiting the length of stride. Preferably the second member also carries a stride limiter for limiting the forward travel of the second member during walking, the stride limiter being mounted on the front face of the second member and acting against a second abutment of the first member. The stride limiter may be cable-operated to a release position permitting the user to sit, and for movement between working and release positions the stride limiter may be pivoted to the second member for rotation about an axis generally normal to the hip pivot shaft.

BRIEF DESCRIPTION OF THE DRAWINGS

An embodiment of the invention will now be described, by way of example only, with reference to the accompanying drawings, in which.

DETAILED DESCRIPTION OF PREFERRED EMBODIMENT

When a hip unit of an artificial leg is attached to a socket, it is necessary to adjust the position of the knee relative to the hip in the medial-lateral (ML) and anterior-posterior (AP) planes. It is also necessary to adjust the angular position of the hip joint when viewed from above. The latter adjustment is needed to control the plane of swing of the limb when walking and also the lateral position of the knee when sitting. In some cases it is necessary to limit the length of the user's stride and in other cases stride length can be controlled by a form of elastic restraint. An object of the invention is to provide a prosthetic hip unit that can meet the above requirements.

Figure 1A:
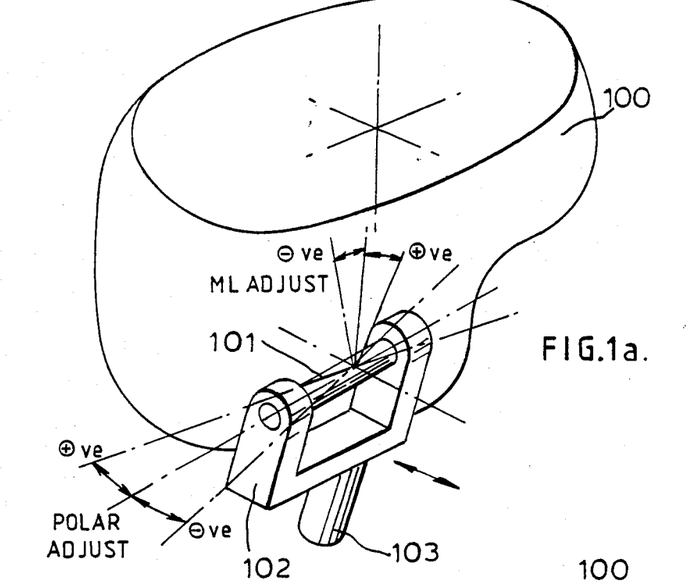
FIG. 1a is a diagrammatic perspective view of a hip unit and a hip disarticulation socket of an artificial leg.
Figure 1B:
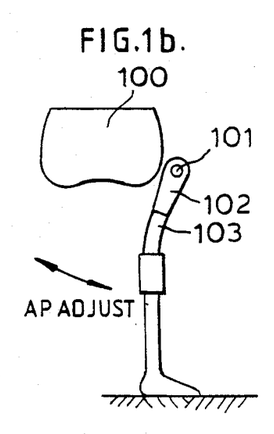
FIGS. 1b, 1c and 1d are side, plan and front views of the leg, hip joint and socket showing the adjustments required.
Figure 1C:
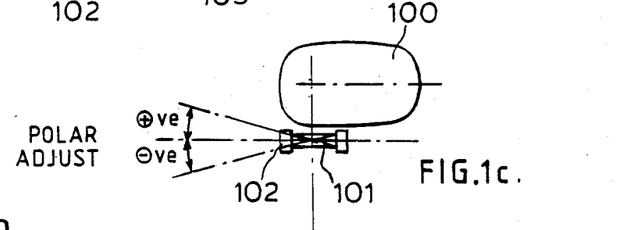
Figure 1D:
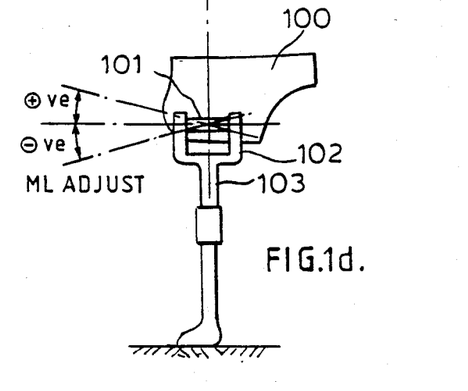
Figures 3, 4, 5:
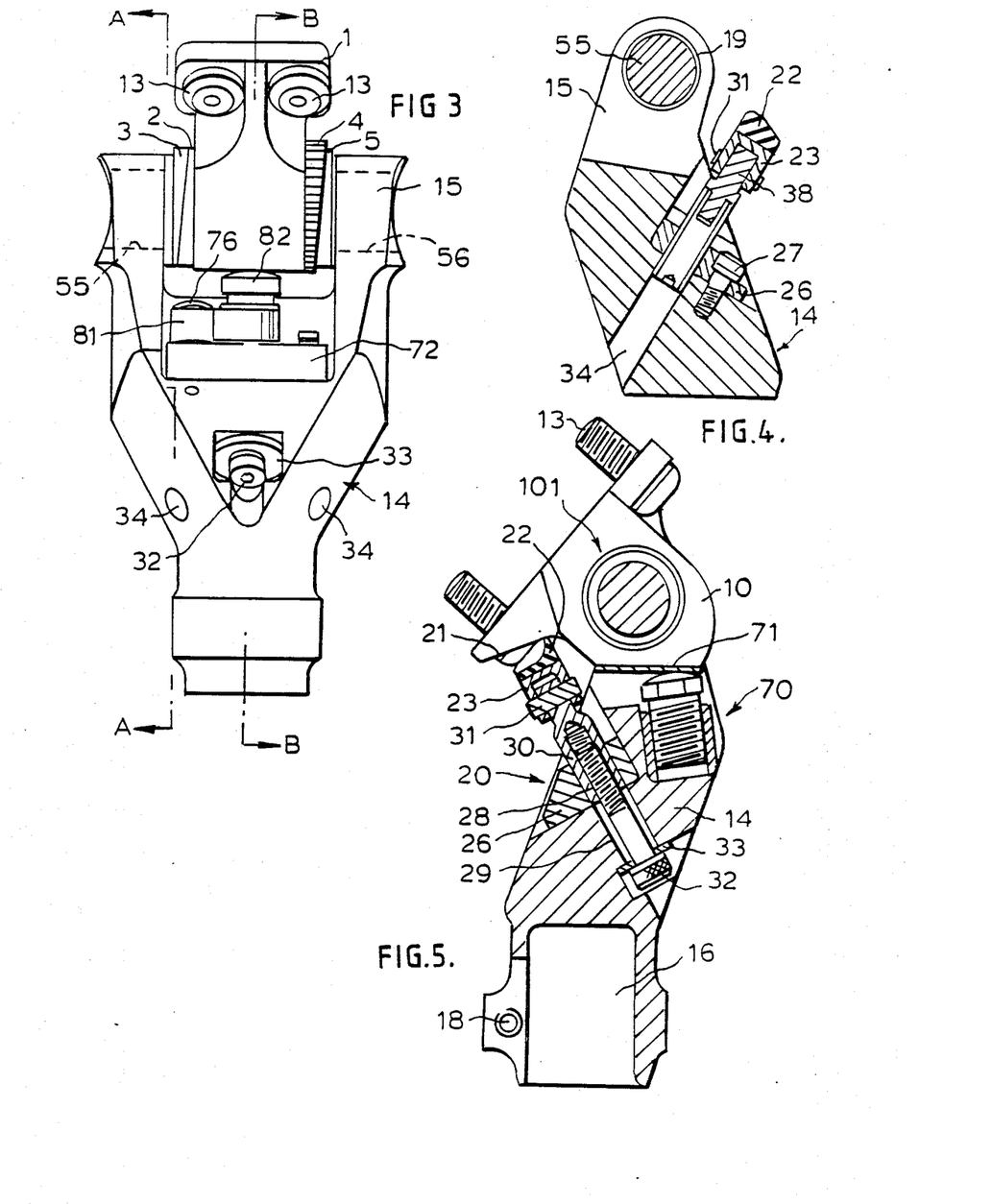
FIG. 3 is a front view of a practical form of the hip joint.
FIGS. 4 and 5 are sections of the hip joint on the lines A—A and B—B of FIG. 3.
Figure 6:
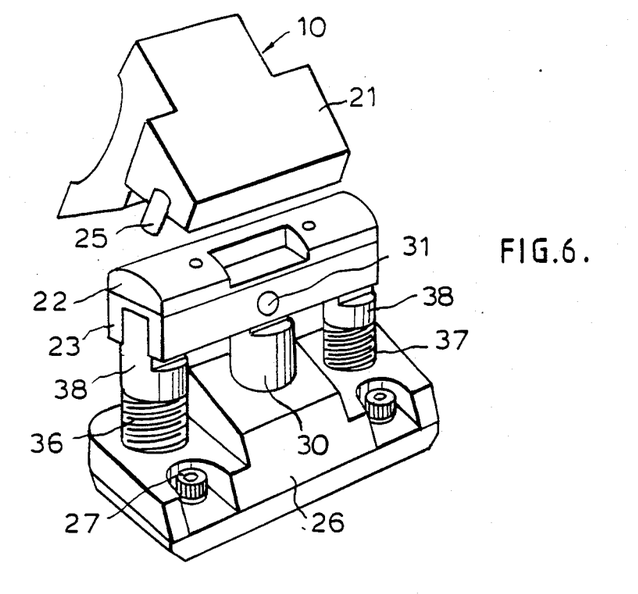
FIG. 6 is a rear view of a buffer mechanism forming part of the hip joint of FIG. 3
Figure 7:
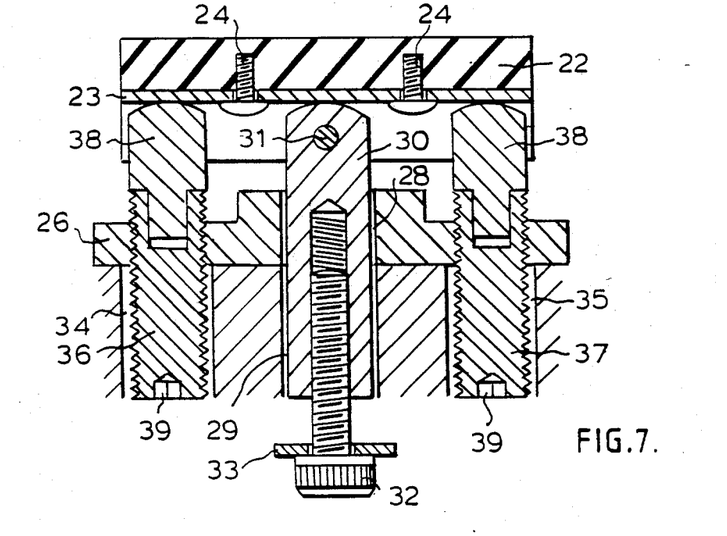
FIG. 7 is a section through a thigh connector fork forming part of the hip joint of FIG. 3 showing components of the buffer mechanism in their working positions.
Figures 8, 9:
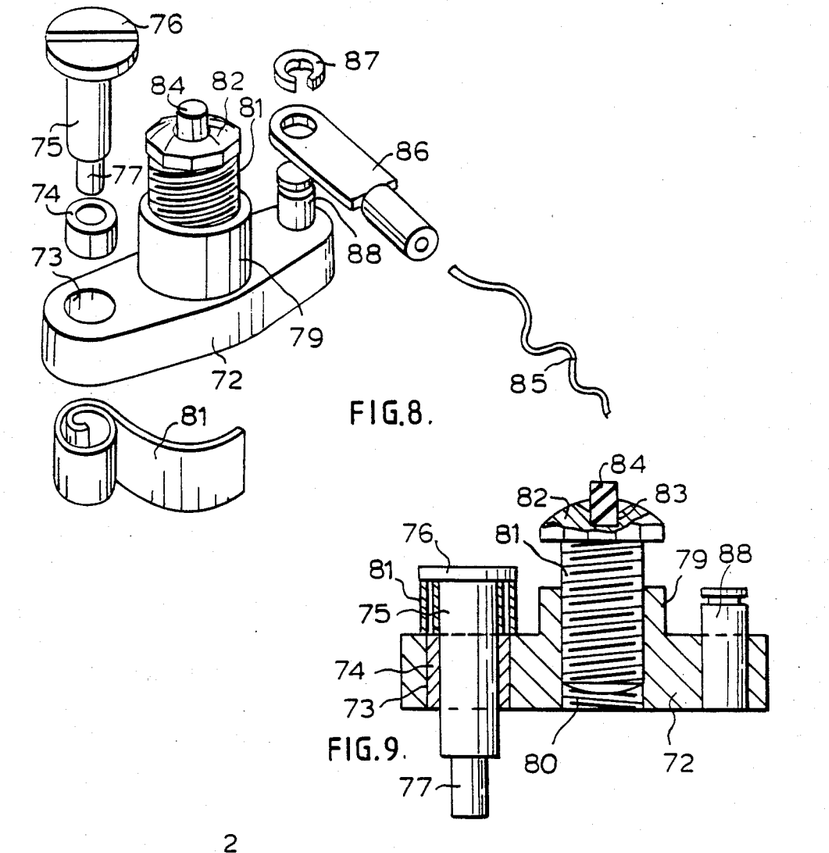
FIG. 8 is an exploded view and FIG. 9 is a vertical section of a stride limiter forming part of the hip joint of FIG. 3.

In FIGS. 1a–1d there is shown in diagrammatic view a hip disarticulation socket 100, a hip pivot shaft 101 and a thigh connector fork 102 connected to a thigh tube 103. The movements needed for adjustments in the AP plane, about a generally vertical or "polar" axis and in the ML plane are shown in FIGS. 1b, 1c and 1d respectively. In FIG. 1a, a positive or negative polar adjustment is made by rotation of the hip pivot shaft 101 about a vertical axis from a reference position parallel to the medial-lateral plane. In FIG. 1b, and AP adjustment is made by rotating a stance position of the thigh tube 103 about the axis of shaft 101. In FIG. 3, a ML adjustment is made by rotating the axis of the hip pivot shaft 101 in a positive or negative direction about a horizontal axis from a horizontal datum position.

Figure 2:
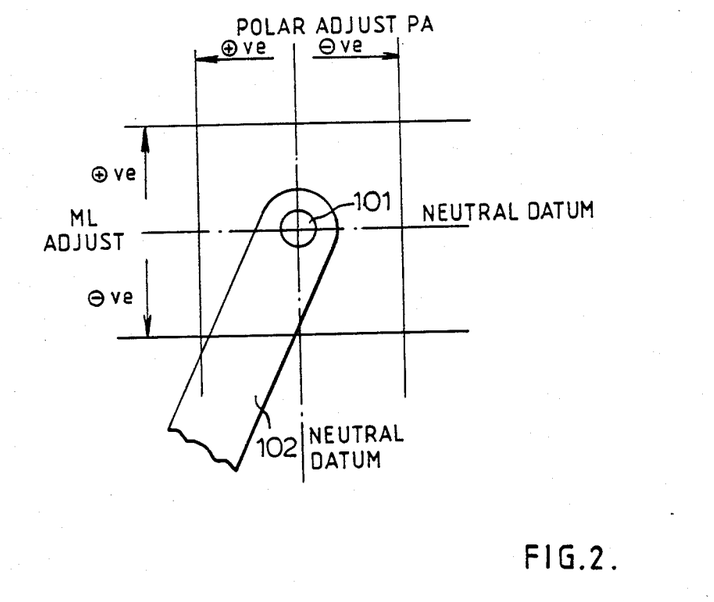
FIG. 2 is a diagram showing how medial-lateral and polar adjustments are related to so-called "absolute angle" and "relative angle"

FIG. 2 is a diagram showing how a polar adjustment angle PA and a medial-lateral adjustment angle MA in Cartesian coordinates are related to a pair of rotations defining a so-called "absolute angle" AA and a so-called "relative angle" AR. The combination of ML and polar adjustments can be expressed in terms of AA which represents the angle through which the axis of the pivot shaft 101 has moved from an initial datum position and AR which is the angle that a plane including the absolute angle makes with a datum plate. It can be shown that:

$$AA = \tan^{-1}[(\tan^2 PA + \tan^2 MA)^{1/2}]$$

$$AR = \tan^{-1}(\tan AM/\tan PA)$$

Any given combination of PA and MA can therefore be transformed into a corresponding combination of AA and AR.

FIGS. 3–5 and 10 show a practical form of the hip joint in which the hip pivot shaft is formed as an assembly of relatively movable components which may be adjusted by a prosthetist to achieve necessary values of AA and AR to give the correct knee position relative to the hip in the patient to which the joint is fitted.

A hip pivot knuckle 10 is formed with a central transverse bore 12 and with a pattern of fixing holes for attachment by screws 13 to the hip disarticulation socket 100. A thigh connector fork generally indicated by the reference numeral 14 has a bifurcated upper end defined by furcations 15 into which the hip pivot knuckle 10 fits. A lower end of the connector fork 14 is formed with a depending slotted thigh tube socket for receiving a thigh tube which can be held in place by tightening a clamping screw 18. The hip pivot knuckle 10 and the thigh connector fork 14 are pivoted together by means of the hip pivot shaft 101 which is formed as a sub-assembly and which fits into the transverse bore 12 and into corresponding holes through the furcations of the thigh connector fork 14 as is conventional in a knuckle joint.

Figure 10:
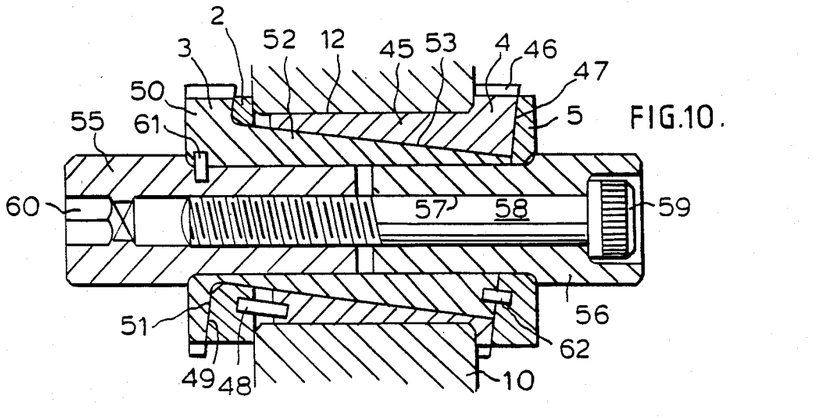
FIG. 10 is a scrap section of a hip pivot knuckle forming part of the hip joint of FIG. 3 with a hip pivot shaft assembly also shown in section.

Referring to FIG. 10, a left hand control bush 4 has a central sleeve portion 45 that is rotatably supported in the transverse central bore 12 and extends from one face to the other thereof. It has a projecting serrated or notched flange 46 permitting it to be rotated by means of a matching spanner-like tool (not shown), the flange 46 butting against a side of the hip pivot knuckle 10 to locate the control bush 4 axially in the central bore 12. The sleeve portion 45 is hollow with an angled bore 53 extending from one end to the other of the control bush 4 and skewed at 5° to an axis defined by the cylindrical outer surface of sleeve portion 45. The flange 46 has an outer face 47 that is correspondingly skewed at 5° to a radial plane. A drive transmission pin 48 extends from an end of the sleeve portion 45 opposite to the flange 46 and is received in an annular washer 2 that fits against the face of the hip pivot knuckle 10 opposite to the flange 46. An outer face 49 of the washer 2 is skewed to lie in a plane parallel to the plane of the outer face 47 of flange 46. A right hand control sleeve generally indicated by the reference numeral 3 has a projecting flange 50. An inner face 51 of the flange 50 butts against and slides over the face 49 of the washer 2. A central sleeve portion 52 of the control sleeve 3 fits into and is rotatable within the skewed bore 53 of the control bush 4. The control bush 4 and control sleeve 3 with the interposed washer 2 are fitted to the hip pivot knuckle 10 before the knuckle 10 is offered to the furcations 15 of thigh connector fork 14. Hollow stub bearing shafts 55,56 are inserted through bushes 19 (FIG. 4) in the furcations 15 so that their reduced diameter inner portions fit into a central axial bore 57 of the control sleeve 3. A cap-headed fixing screw 58 is inserted into the bearing shaft 56 which has a counterbore into which its head 59 fits. A left hand wasaher 5 having an inclined inner face fits onto the bearing shaft 56 between a slightly enlarged head thereof and end flange 46 of the left hand control bush 4. A pin 62 connects the washer 5 and right hand control sleeve 3 so that they rotate together. The internal bore of shaft 56 is plain and receives a plain region of the screw 58, whereas the internal bore of shaft 55 is threaded and receives a threaded end of the screw 58, so that the screw 58 clamps the bearing shaft 55,56 together and holds together the resulting assembly defining the hip pivot shaft 101.

The outer face of the right hand bearing shaft 55 is formed with a drive socket 60 to receive a hexagonal or otherwise profiled key by which it may be rotated, the rotation being transmitted by a pin 61 to the right hand control sleeve 3 and in turn by the projecting pin 62 of the control sleeve 3 to the left hand washer 5. Thus washer 2, together with sleeve portion 45 and flange 46 of left hand control bush 4 constitute an inner spool coupled by drive transmission pin 48 to rotate as a unit. Flange 50 and central sleeve 52 of right hand control sleeve 3 together with washer 5 constitute an outer spool that traps the inner spool between its ends with a central skewed bearing shaft that passes through a sleeve defined by portion 45 of the inner spool. The inner spool carries bearing shafts 55,56 which are coaxial and whose common axis defines the axis of the hip pivot shaft 101. A required combination of absolute and relative angles is set by adjusting the rotational positions of the right hand control sleeve 3 and the left hand control bush 4, after which the cap head screw 58 is tightened to lock the spools solid with the hip pivot knuckle 10. The hip pivot action is then between the extremities of the shafts 55,56 and the furcations 15 of the thigh connector fork 14.

In the position shown in FIG. 10, the journal bearings defined by the inner and outer spools 2,4 and 3,5 are in a neutral position corresponding to a neutral adjustment in its medial-lateral and polar planes. If the inner spool 3,5 carrying the pivot shafts 55,56 is moved angularly by 180 degrees relative to the outer spool or sleeve 2,4 the bearing shafts 55,56 adopt an angle 2B where B is the angle that the inner spool 3,5 makes with the axis of the outer spoool 2,4. Thus, by changing the angle between the inner spool 3,5 and the outer spool 2,4 any absolute angle AA between the bearing shafts 55,56 and the central bore 12 of the hip pivot knuckle 10 can be achieved from zero to 2B. Thus, in a first step towards setting up a required combination of absolute and relative angle AA and AR to achieve a given adjustment, the inner and outer sleeves 2,4 and 3,5 are rotated to an appropriate angular position relative to one another. It can be shown that if C represents an angle that the inner spool 3,5 has been rotated relative to the outer spool 2,4, then:

Absolute angle achieved $= 2 \sin^{-1}[\sin B . \sin (C/2)]$

Relative angle achieved $= C/2$

Figure 11A:
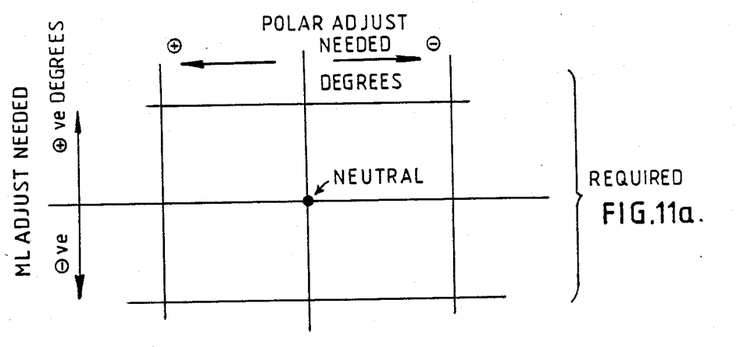
FIGS. 11a–11c are diagrams exemplifying materials that could be used by a prosthetist to enable him to determine how to position the components of the hip pivot shaft assembly to achieve required values of angles PA and MA referred to below.
Figure 11B:
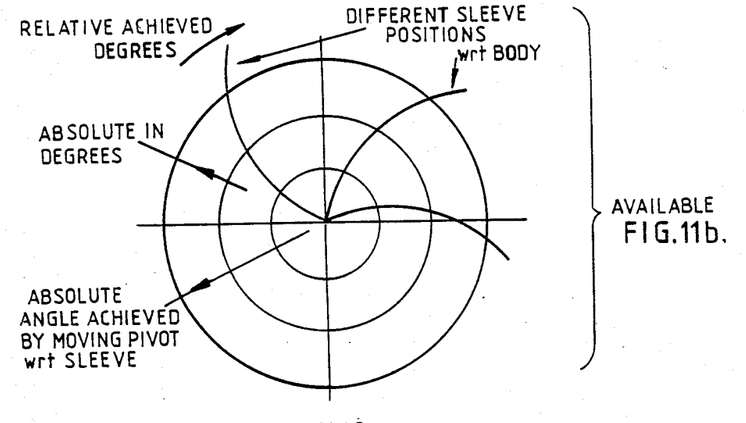
Figure 11C:
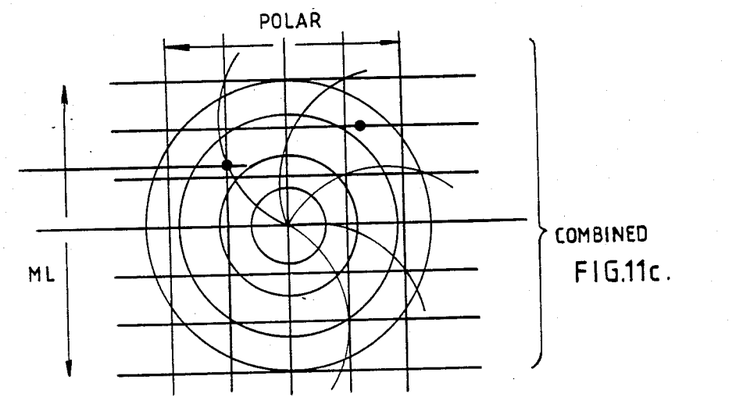

The next step is to rotate the complete assembly of the two bearing shafts 55,56 and spools 2,4 and 3,5 relative to the pivot knuckle 10. When this is done, the absolute angle AA remains unchanged, but the realtive angle AR may be set to any desired value. Any combination of ML and polar adjustments defined by angles PA and MA can be expressed in terms of absolute and relative angles AA and AR and that combination of angles AA and AR can be obtained by relative rotation of the inner spool 3,5 and outer spool 2,4. The determination of the appropriate values of AA and AR wanted for a particular patient by his prosthetist can be made either using the mathematical relationships described above or, more conveniently, by using the graphical method shown in FIGS. 11a to 11c. In FIG. 11a, the range of positive and negative adjustments in angle PA and positive and negative adjustments in medial-lateral adjustment angle MA are plotted using Cartesian coordinates starting from a neutral datum position. A required attitude of the hip pivot shaft 101 in terms of the angles angles PA and MA is plotted on that graph which may conveniently be in the form of a transparent overlay. In FIG. 11b, a series of concentric circles each represents an absolute angle AA achieved by a given relative position of the inner and outer spools 3,5 and 2,4 and a series of curves or lines diverging from the common centre of the circles represents a relative angle AR in degrees corresponding to a particular rotational position of the outer spool 3,5 relative to the hip pivot knuckle 10. By superimposing the Cartesian graph of FIG. 11a on the polar graph of FIG. 11b, it is possible to read off directly the angles AA and AR corresponding to a desired PA and MA.

Referring in particular to FIGS. 4-7, the thigh connector fork 14 carries a buffer assembly 20 that contacts an abutment 21 of the hip pivot knuckle 10 to define a rearward limit of swing of the thigh tube 103. The buffer assembly 20 has to meet a number of requirements if it is to be fully satisfactory. The rearward limit of swing of the thigh tube 103 has to be adjustable through an adequate range and the assembly 20 has to accomoodate the range of attitudes that the thigh connector fork 14 can take up relative to the hip pivot knuckle as the angles AA and AR are varied. The assembly 20 has also to be sufficiently robust. These subsidiary problems are solved, according to a preferred aspect of the invention, by providing a medially-laterally directed buffer bar having a pivot at its centre, a first screw jack in the thigh connector fork 14 having an end connected by the pivot to the buffer bar, extension or retraction of the first screw jack varying the distance of the buffer bar pivot from the thigh connector fork 14, and second and third screw jacks in the thigh connector fork 14 to either side of the first screw jack acting adjacent the ends of the buffer bar, the arrangement being such that with the first screw jack extended the attitude of the buffer bar can be set parallel to the plane of the abutment 21 of the hip pivot knuckle 10 by extension or retraction of the second and third screw jacks, and the first screw jack can be retightened to hold the buffer bar in compression against the second and third screw jacks.

In FIGS. 4-7, a hard rubber buffer shoe 22 is attached by means of screws 24 to a sleeper 23 which is an elongated member of channel section directed medially-laterally. At the rearward extremity of travel of thigh tube 103 the buffer shoe 22 contacts the abutment 21 into which are let soft rubber buffers 25 for the purpose of absorbing the impact and of sound deadening. The rear face of the thigh connector fork 14 is formed with a cut-out into which a buffer mounting block 26 is attached by screws 27. The buffer mounting block 26 is formed with a central through hole 28 that aligns with a hole 29 in the thigh connector fork 14 and receives an internally threaded sleeve 30. The sleeve 30 is a sliding fit in the holes 28,29 which together define a posteriorly and upwardly inclined bore extending from front to back of the thigh connector fork 14. A pin 31 pivotally connects the sleeper 23 to the sleeve 30. A cap screw 32 inserted from the front of the thigh connector fork 14 into the hole 29 threadedly engages the sleeve 30 and defines therewith the first screw jack. At the forward end of the bore, the head of cap screw 32 is trapped by washer 33, the screw 32 when tightened pulling the sleeper 23 forwardly and downwardly. Left hand and right hand buffer adjustment screws 36, 37 fit into posteriorly and upwardly inclined plain bore 34 through thigh connector fork 14 and threaded bores 35 through buffer mounting block 26 to form the second and third screw jacks. Their upper ends carry spigots that engage into the sleeper 23 and their lower ends are formed with screwdriver of key sockets 39. Extension or retraction of the adjustment screws 36,37 with the first screw jack defined by sleeve 30 and cap screw 32 extended allows the sleeper 23 to be tilted on its pivot pin 31 so that it is parallel to the abutment 21 at the selected values of angles AA and AR. When the correctly parallel attitude of the sleeper 23 has been set, the cap screw 32 is tightened to return the sleeper 23 towards the buffer mounting block 26 and lock the sleeper 23 firmly against the ends of spigots 38. It will be noted that the buffer shoe 22 is convexly curved when viewed in side profile so that line contact is always achievable with the abutment 21 on the thigh connector fork 14. The above buffer mechanism permits the position of the hip fork 14 and thigh tube 103 at the rearmost limit of leg swing to be adjusted through a 20° range of travel.

The above described hip unit has a stride limiter for limiting the forward travel of the thigh tube 103 during walking. Referring to FIGS. 3, 5, 8 and 9, the stride limiter 70 is mounted on the front face of the thigh connector fork 14 and acts against a second abutment 71 of the hip pivot knuckle 10. The front face of the connector fork 10 is cut away to receive a carrier bar 72 formed adjacent one end with a through hole 73 in which there fits a sleeve 74. The carrier bar 72 rests on and is pivoted to the thigh connector fork 14 for rotation about a generally vertical axis towards or away from the connector fork 14 by means of a pivot pin 76 having a plain upper region 75 that passes through the bush 74 and having a stepped lower end 77 that is an interference fit into a blind bore (not shown) in the thigh connector fork 14. Midway along its length the carrier bar 72 has an upstanding spigot 79 formed with a threaded internal bore 80. A leaf spring 81 is retained on the plain region 75 of the pivot pin 76 above the carrier bar 72 and engages against the spigot 79 to urge the carrier bar 72 towards the thigh connector fork 14. A buffer screw 81 fits into the threaded bore 80 and has a head 82 formed with a blind bore 83 in which a buffer rubber 84 is a compression fit. In a working position of the stride limiter 70 against the thigh connector fork 14, the buffer rubber 84 and buffer screw head 82 contact the second abutment 71 at each forward swing of the thigh tube 103 to limit the forward stride, load being transmitted from the hip pivot knuckle 10 through the buffer screw 81 and carrier bar 72 into the thigh connector fork 14. The carrier bar 72 may be pivoted away from the thigh connector fork 14 so as to free buffer screw 81 from beneath the second abutment 71 and thereby enable the patient to sit down. This is done by pull on a release cable 85 connected by pivoting link 86 to pin 88 upstanding from the free end of carrier bar 72. The link 86 is retained on the pin 88 by circlip 87.

The above hip joint has a number of advantages in addition to angular adjustability. The repositioning of the stride limiter 70 on the thigh connector fork 14 provides for up to 15° more movement compared to a previous artifical hip joint made by the applicants in which the stride limiter was carried by the hip pivot part of the joint. The buffer assembly 70 is adjustable for both stance position and for attitude of the hip pivot shaft 101. The multi-component hip pivot shaft 101 enables the thigh connector fork to be made from a single piece of metal, the control sleeves 3,4 and washers 2,5 making up the inner and outer spools 3,5 and 2,4 being split to enable assembly but clamping solid with the bearing shafts 55,56 when the capheaded screw 58 is tightened.

It will be appreciated that modifications may be made to the embodiment described above without departing from the invention, the scope of which is defined in the appended claims.

I claim:
1. A hip joint for a prosthetic leg, wherein first and second members are pivoted together by a pin extending through the first member, the pin including outer spindle means rotatable in a bearing in said first member and inner spindle means rotatable in a bearing in said outer spindle means and carrying pivot means for said second member, wherein said inner spindle means is also in said first member, said inner spindle means having an axis skew to the outer spindle means so that, firstly, an angle between the pivot axis of the joint and said first member may be set by adjusting the relative angular positions of said inner and outer spindle means, and secondly, an attitude of said pivot axis may be set by adjusting the angular position of said outer spindle means relative to said first member, the pivot means including means for preventing rotation of the inner and outer spindle means once the said relative positions have been set.

2. A hip joint according to claim 1, wherein the first member is a knuckle and the second member is a fork connected to the knuckle by the pin.

3. A hip joint according to claim 2, wherein a base of the fork has a socket in which a thigh tube of the prosthetic leg is receivable in use.

4. A hip joint according to claim 1, wherein the outer spindle means is in the form of a spool having flanges that locate against the first member at opposed ends of the bearing therein, and the inner spindle means is also in the form of a spool having flanges that locate against the flanges of the outer spindle means.

5. A hip joint according to claim 4, wherein said outer spindle means and said inner spindle means are each formed in two complementary parts that fit together from opposed sides of the bearing in the first member, means coupling the complementary parts so that they rotate together.

6. A hip joint according to claim 5, wherein one complementary part is a flanged sleeve and the other complementary part is a washer.

7. A hip joint according to claim 1, wherein the second member also carries a stride limiter for limiting the forward travel of the second member during walking, and stride limiter being mounted on the front face of the second member and acting against a second abutment of the first member.

8. A hip joint according to claim 7, wherein the stride limiter is pivoted to the second member for rotation about an axis generally normal to the hip pivot shaft.

9. A hip joint as claimed in claim 1, wherein the means for preventing rotation of the inner and outer spindle means comprises a compression means operative to clamp said spindle means together.

10. A hip joint as claimed in claim 9, wherein the inner spindle means has a bore in which a pair of stub shafts fit, means retaining the stub shafts in the bore, said stub shafts fitting into bearings in the second member.

11. A hip joint as claimed in claim 10, wherein the retaining means is a screw inserted through a bore in one stub shaft into a threaded bore in the other stub shaft.

12. A hip joint according to claim 11, wherein said other stub shaft is coupled to the inner spindle means for rotation therewith and has a formation for receiving a tool by which said stub shaft may be rotated.

13. A hip joint according to claim 1, wherein the second member carries buffer means that contacts an abutment on the first member at a contact line or plane to define a rearward limit of swing of the second member, the buffer means having first adjustment means by which a limit of swing of the second member can be set, and second adjustment means by which a line or plane or action of the buffer means can be aligned with the abutment on the first member.

14. A hip joint according to claim 13, wherein the second member has a medially-laterally directed buffer bar having a pivot at its centre, a first screw jack having an end connected by the pivot to the buffer bar, extension or retraction of the first screw jack varying the distance of the buffer bar pivot from the second member, and second and third screw jacks in the second member to either side of the first screw jack acting adjacent the ends of the buffer bar, the arrangement being such that with the first screw jack extended the attitude of the buffer bar can be set parallel to the plane of the abutment of the first member by extension or retraction of the second and third screw jacks, and the first screw jack can be retightened to hold the buffer bar in compression against the second and third screw jacks.

15. A hip joint according to claim 14, wherein the buffer bar carries a buffer shoe of elastomeric material that is convexly curved when viewed in profile.

16. A hip joint according to claim 14, wherein the second member has a front face and first second and third bores opening into said front face into which said first, second and third screw jacks fit, each screw jack having a socket formation by which it may be rotated and accessible from the front face of the second member.

* * * * *